US010933200B2

United States Patent
Chassot et al.

(10) Patent No.: US 10,933,200 B2
(45) Date of Patent: Mar. 2, 2021

(54) THERMAL CONDITIONING DEVICE FOR AN INJECTION SYSTEM

(71) Applicant: Bracco Injeneering SA, Lausanne (CH)

(72) Inventors: Pierre Yves Chassot, Thoiry (FR); Nicolas Pawelczyk, Geneva (CH)

(73) Assignee: ACIST Medical Systems, Inc., Eden Prairie, MN (US)

( * ) Notice: Subject to any disclaimer, the term of this patent is extended or adjusted under 35 U.S.C. 154(b) by 279 days.

(21) Appl. No.: 16/067,342

(22) PCT Filed: Dec. 21, 2016

(86) PCT No.: PCT/EP2016/082141
§ 371 (c)(1),
(2) Date: Jun. 29, 2018

(87) PCT Pub. No.: WO2017/114718
PCT Pub. Date: Jul. 6, 2017

(65) Prior Publication Data
US 2019/0015603 A1 Jan. 17, 2019

(30) Foreign Application Priority Data
Dec. 30, 2015 (EP) .................................... 15203123

(51) Int. Cl.
*A61M 5/44* (2006.01)
*A61M 5/00* (2006.01)
(Continued)

(52) U.S. Cl.
CPC ............ *A61M 5/445* (2013.01); *A61M 5/007* (2013.01); *A61M 5/1408* (2013.01);
(Continued)

(58) Field of Classification Search
CPC ........ A61M 5/44; A61M 5/445; A61M 5/007; A61M 5/1408; A61M 5/1407;
(Continued)

(56) References Cited

U.S. PATENT DOCUMENTS 2,470,481 A  5/1949  Ethelyn
3,619,563 A  * 11/1971  Hirst .................. A47J 36/2483
                                                    219/386
(Continued)

FOREIGN PATENT DOCUMENTS

RU    2308865 C2    10/2007
WO    2010051205 A2  5/2010

OTHER PUBLICATIONS

PCT Search Report and Written Opinion for PCT/EP2016/082141, dated Mar. 21, 2017.

*Primary Examiner* — Nathan R Price
*Assistant Examiner* — Dung T Ulsh
(74) *Attorney, Agent, or Firm* — Vivicar Law, PLLC

(57) ABSTRACT

A solution for injecting one or more fluids into a patient is proposed. A corresponding injection system (200) comprises one or more supply stations (105a;105b) each one for supplying one of the fluids to be injected from a container (110a;110b); at least one of the supply stations (105a;105b) comprises housing means (115a, 120a;115b, 120b) defining a chamber for housing the container (110a;110b), the chamber having a connection port (132a;132b) for connecting the
(Continued)

container (110*a*; 110*b*) to a delivery arrangement (135,145) for delivering the fluid to the patient, and a conditioning device (205*a;*205*b*) for thermally conditioning the fluid in the chamber, wherein the conditioning device (205*a;*205*b*) comprises a first conditioning element (210*a;*210*b*) arranged around the connection port (132*a;*132*b*) and a second conditioning element (215;215*a;*215*b*) extending transversally to the first conditioning element (210;210*a;*210*b*).

20 Claims, 5 Drawing Sheets

(51) Int. Cl.
*A61M 5/14* (2006.01)
*A61M 5/172* (2006.01)
(52) U.S. Cl.
CPC ... *A61M 5/1723* (2013.01); *A61M 2205/3368* (2013.01); *A61M 2205/3653* (2013.01)
(58) Field of Classification Search
CPC ........ A61M 5/1723; A61M 2205/3368; A61M 2205/36; A61M 2206/3653; A61J 2200/42; A61J 2200/40; A47J 36/24; A47J 36/2411; A47J 36/2433; A47J 36/2483
See application file for complete search history.

(56) References Cited

U.S. PATENT DOCUMENTS

| | | | | |
|---|---|---|---|---|
| 4,249,923 | A * | 2/1981 | Walda | A61B 18/02 165/169 |
| 5,210,396 | A * | 5/1993 | Sanders | A47J 36/2483 219/386 |
| 6,906,289 | B2 | 6/2005 | Vives et al. | |
| 8,463,362 | B2 | 6/2013 | Fago | |
| 9,101,705 | B2 | 8/2015 | Rhinehart et al. | |
| 2006/0086361 | A1* | 4/2006 | Kammer | A61M 3/0245 128/849 |
| 2006/0153549 | A1* | 7/2006 | Cazzini | A61M 5/445 392/470 |
| 2007/0225639 | A1* | 9/2007 | Azzolini | A61M 5/1414 604/80 |
| 2008/0113306 | A1* | 5/2008 | Veasey | F23N 5/006 431/6 |
| 2011/0062149 | A1* | 3/2011 | Driel | A47J 36/2433 219/618 |
| 2011/0166517 | A1* | 7/2011 | Blakeley | A61M 5/445 604/113 |
| 2011/0184501 | A1 | 7/2011 | Gill et al. | |
| 2011/0208047 | A1* | 8/2011 | Fago | A61M 5/14546 600/432 |
| 2014/0069606 | A1* | 3/2014 | Lee | A61J 9/001 165/63 |
| 2014/0091083 | A1* | 4/2014 | McGarvey | H05B 6/36 219/634 |

\* cited by examiner

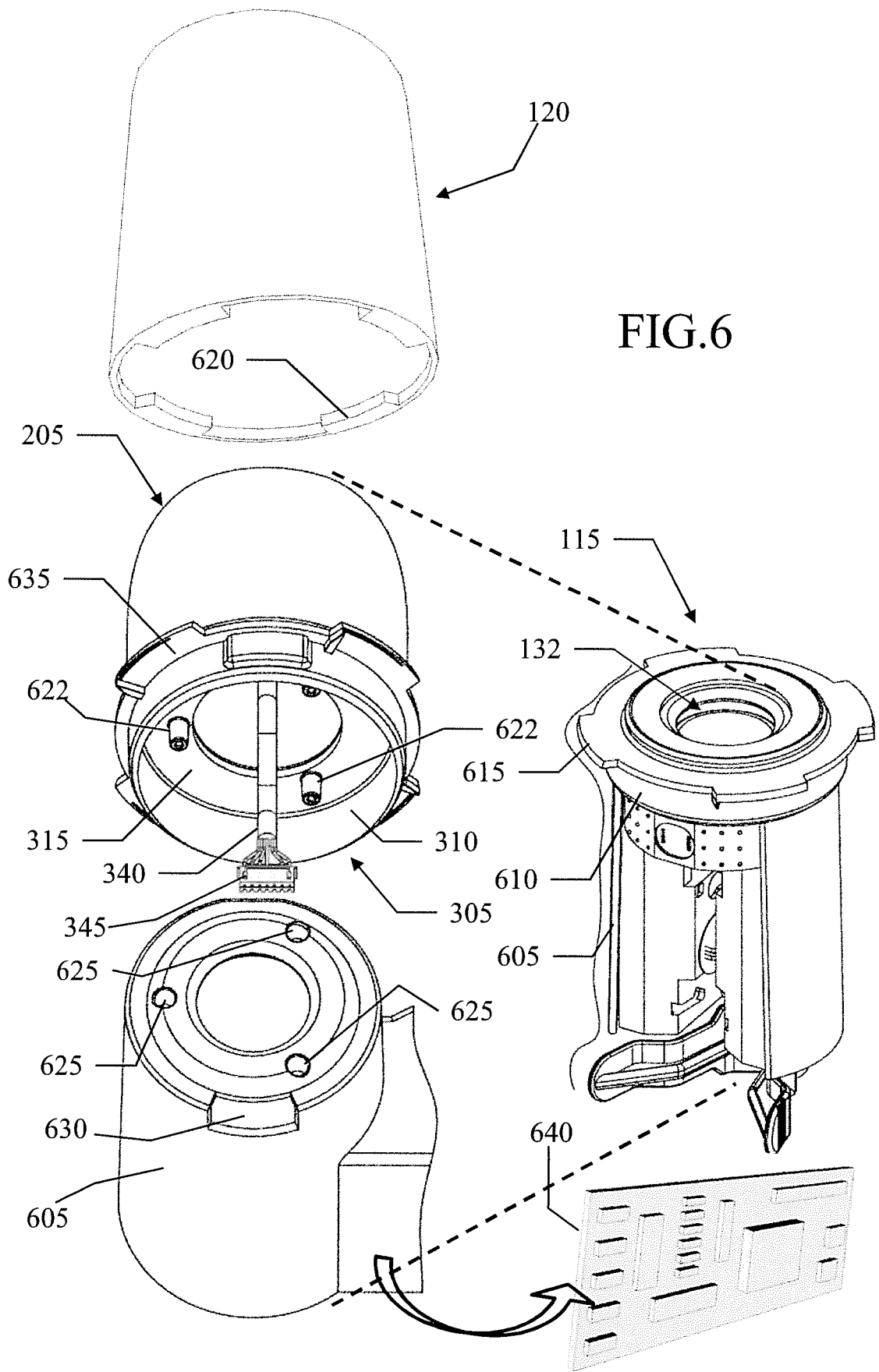

THERMAL CONDITIONING DEVICE FOR AN INJECTION SYSTEM

CROSS-REFERENCE TO RELATED APPLICATIONS

This application is the national stage application of corresponding international application number PCT/EP2016/082141, filed Dec. 21, 2016, which claims priority to and the benefit of European application no. 15203123.3, filed Dec. 30, 2015, all of which are hereby incorporated by reference in their entirety.

TECHNICAL FIELD

The present disclosure relates to the field of medical equipment. More specifically, this disclosure relates to injection systems.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients in scan examinations thereof. Particularly, in imaging applications (wherein a visual representation of the interior of the patients is created in a non-invasive way without turning to surgery techniques) the use of the contrast agent makes the target features more conspicuous. As a result, target features that would otherwise be less distinguishable from other nearby features (for example, surrounding tissues) are highlighted. This significantly facilitates the task of clinicians in diagnostic applications, and particularly the identification and/or characterization of lesions, the monitoring of their evolution or response to medical treatments. For example, a iodine-based contrast agent (such as comprising iopamidol) is commonly used in Computed Tomography (CT) applications (such as for angiography investigations).

The contrast agent is usually injected into a blood vessel of a patient by an (automated) injection system. The injection system pressurizes the contrast agent (supplied from a corresponding container) and injects it into the patient under predetermined injection conditions, for example, at a predetermined flow rate and volume. In this way, the contrast agent may be injected in a controlled, safe and efficient manner.

Typically, the contrast agent has a relatively high viscosity. The viscosity of the contrast agent may adversely affect its correct injection in the patient (for example, since occurring at a flow rate lower than it is desired); in any case, this requires the application of a relatively high pressure (with an increase in complexity, and then cost, of the injection system). Moreover, the injection of the contrast agent with high viscosity and at high pressure is quite uncomfortable for the patient.

The viscosity of most contrast agents may be reduced by increasing their temperature. Therefore, the contrast agent is generally pre-warmed before being injected by using a dedicated equipment (for example, a warmer) separated from the injection system. For example, contrast agents pre-warmed to a target temperature close to the body temperature (such as 35-37° C.) may halve their viscosity. In this way, it is easier to inject the contrast agent efficiently (for example, at the desired flow rate) with lower pressure (and then lower complexity and cost of the injection system) and higher comfort for the patient.

However, the contrast agent cools quite fast and then accordingly increases its viscosity immediately before and/or during the injection. Therefore, in some injection systems the container of the contrast agent is housed in a dedicated chamber, which provides for a thermal insulation thereof. In any case, the inevitable heat loss does not allow maintaining the target temperature of the contrast agent for the entire scan examination (i.e., an imaging procedure).

In order to mitigate the cooling of the contrast agent, some injection systems are provided with a heating device that is controlled to warm the contrast agent to be injected, so as to maintain it at the target temperature during the whole scan examination. For example, U.S. Pat. No. 9,101,705 proposes a bulk fluid heating system in operative connection with the container and an inline, real time heating system in operative connection with the fluid path. Moreover, U.S. Pat. No. 8,463,362 proposes a bulk fluid container holder module including one or more resistive elements disposed along one or more surfaces of the container holders. The container holders may cradle bottles inserted therein (with surfaces of the container holders corresponding to portions of the shape of the bottles), resulting in a contact area that may aid the transfer of heat from the container holders to the bottles.

Alternatively, the heating device may be implemented by resistive elements that are embedded in a protective cover of the chamber housing the container of the contrast agent or in a vertical plate arranged therein.

However, the performance of these configurations is not completely satisfactory; moreover, they require a complete redesign of the injection system.

U.S. Pat. No. 2,470,481 discloses a fluid heater for containers of intravenous injections of glucose or saline solutions, and blood plasma. The heater comprises spaced walls with heating elements there between. A heat transfer element connects with a thermostat and the heating elements are controlled by the thermostat to maintain the temperature at the proper set level.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of using two thermal conditioning elements (i.e. two heating elements).

Particularly, an aspect provides an injection system wherein in at least one supply station a conditioning device (i.e. a heating device, for thermally conditioning a fluid in a corresponding chamber) is present and it comprises a first conditioning element (i.e. a first heating element, which is arranged around a connection port for connecting a container of the fluid) and a second conditioning element (i.e. a second heating element, which extends transversally to the first conditioning element).

A further aspect provides a corresponding method for operating said injection system.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly:

FIG. 6 shows an exemplary installation of the heating device according to an embodiment of the present disclosure.

DETAILED DESCRIPTION

Figure 1:
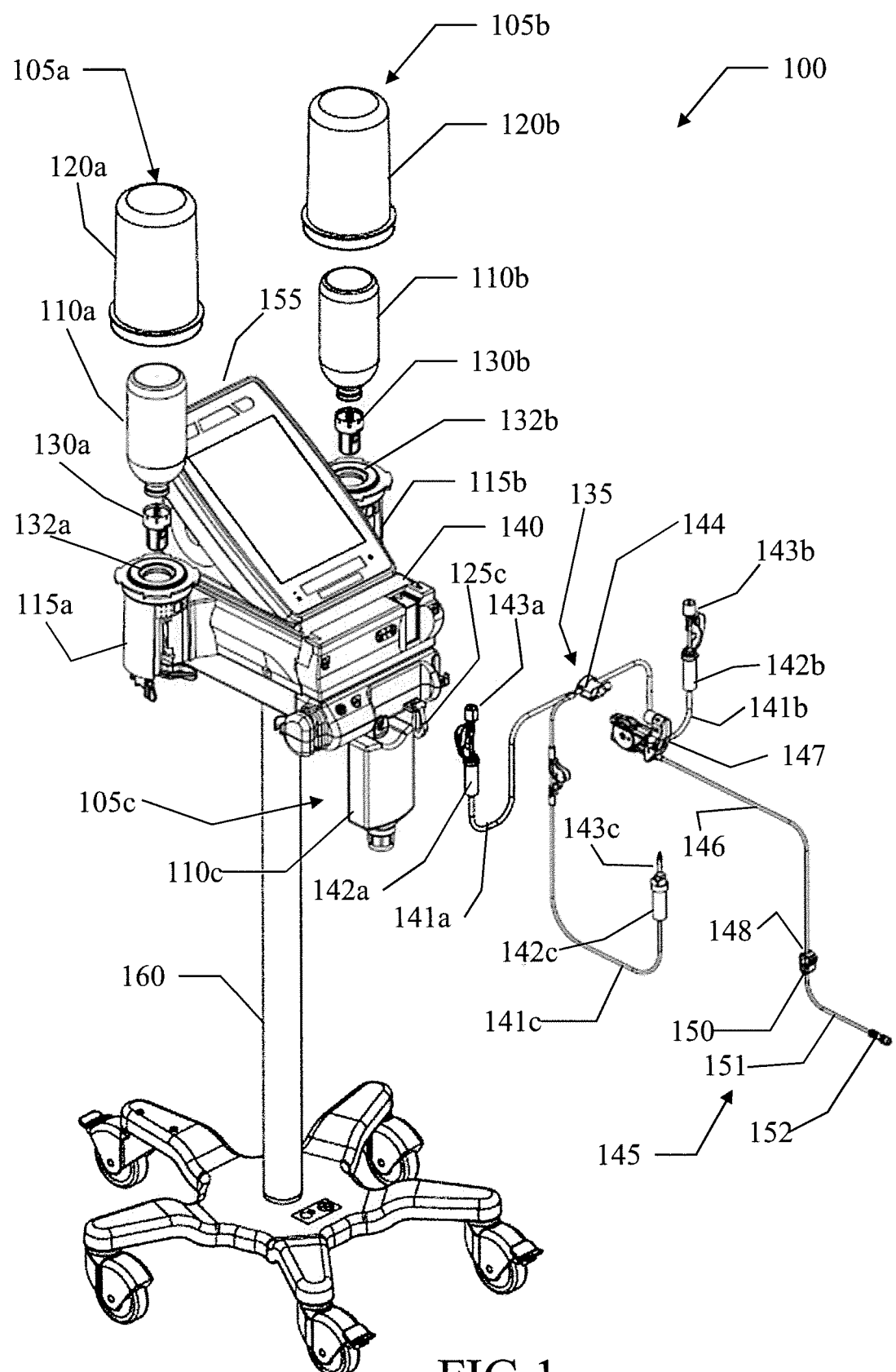
FIG. 1 shows a pictorial representation in partially exploded view of an injection system wherein the solution according to an embodiment of the present disclosure (not shown in the figure) may be applied.

With reference in particular to FIG. 1, a pictorial representation in partial exploded view is shown of an injection system 100 wherein the solution according to an embodiment of the present disclosure (not shown in the figure) may be applied.

The injection system 100 is used to inject one or more medical fluids into a patient (not shown in the figure); particularly, the injection system 100 is an (automatic) contrast agent and saline solution (syringe-less) injector that is used by clinicians to perform scan examinations (for example, in radiography applications like CT applications).

The injection system 100 comprises a (left) supply station 105a, a (right) supply station 105b and a (front) supply station 105c for supplying the medical fluids to be injected from corresponding containers. Particularly, the supply station 105a and the supply station 105b supply a medical fluid from a bottle 110a and from a bottle 110b, respectively (for example, made of glass or rigid plastic), whereas the supply station 105c supplies a medical fluid from a pouch 110c (for example, made of soft plastic). The supply stations 105a, 105b may be used to supply one or more contrast agents (to enhance contrast of specific body features within the patient) or a contrast agent and a saline solution (comprising a physiological or isotonic solution), whereas the supply station 105c may be used to supply the saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE manufactured by Bracco Diagnostics Inc. (trademarks). Each bottle 110a,110b may contain a single or multiple dose (for example, 50-500 ml) of different contrast agents (to be supplied in a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to obtain a mixing of the contrast agent and the saline solution within an organ of the patient, for example, the heart). Alternatively, the supply stations 105a and 105b may be used to supply a contrast agent and a saline solution, respectively (without the use of the supply station 105c).

More specifically, each supply station 105a,105b (respectively) comprises a bottle holder 115a,115b for the bottle 110a,110b. A protective cover 120a,120b is mounted on the bottle holder 115a,115b to cover the bottle 110a,110b when it is held thereon, thereby defining a closed chamber for housing the bottle 110a,110b. The bottle holder 115a,115b in combination with the protective cover 120a,120b defines a housing means for receiving the bottle 110a,110b. The bottle holder 115a,115b and the protective cover 120a,120b protect the bottle 110a,110b from external accidental shocks. Moreover, they are made of a thermally insulating material (for example, polycarbonate) to reduce heat losses, thereby helping to maintain warm (for example, at about the body temperature) the medical fluid contained in the bottle 110a, 110b. In fact, the protective cover 120a,120b associated to the respective bottle holder 115a,115b defines a closed chamber which is separated from the external environment and which thermally insulates the bottle 110a,110b from the external environment. The supply station 105c instead simply comprises a hook 125c for hanging the pouch 110c.

A delivery arrangement creates a completely closed fluid pathway for delivering the medical fluids from the containers 110a,110b,110c to the patient.

For this purpose, in each supply station 105a,105b a bottle connector 130a,130b is arranged in a connection port 132a, 132b of the bottle holder 115a,115b. The bottle connector 130a,130b comprises a spike for connecting to the bottle 110a,110b and a connection element (for example, a septum or a male luer lock fitting) in fluid connection with the spike. The spike and the connection element are located at opposite longitudinal ends of the bottle connector 130a,130b. Typically, the bottle connector 130a,130b also comprises a filtering unit (not shown in the figure) between its spike and connection element. The bottle connector 130a,130b is a disposable element for use with a single bottle 110a,110b (for example, with the spike that breaks off and remains inside the bottle 110a,110b when the bottle connector 130a, 130b is removed to prevent any accidental re-use thereof).

A transfer set 135 connects all the supply stations 105a, 105b, 105c to a pressurizing unit 140 for transferring the corresponding medical fluids from the containers 110a, 110b, 110c to the pressurizing unit 140. The transfer set 135 comprises a transfer line for each supply station 105a, 105b, 105c. The transfer line of each supply station 105a, 105b comprises a flexible tube 141a, 141b that is provided (at a distal end thereof with respect to the pressurizing unit 140) with a reservoir (or drip chamber) 142a, 142b and a connection element 143a, 143b for mating with the connection element of the bottle connector 130a, 130b. For example, the connection element 143a, 143b is a spike in case the connection element of the bottle connector 130a, 130b is a septum, or the connection element 143a, 143b is a female luer lock fitting in case the connection element of the bottle connector 130a, 130b is a male luer fitting. The reservoir 142, a142b and the connection element 143a, 143b are arranged inside the bottle holder 115a, 115b. The transfer line of the supply station 105c comprises a flexible tube 141c that is provided (at a distal end thereof with respect to the pressurizing unit 140) with a reservoir (or drip chamber) 142c and a spike 143c for connecting to the pouch 110c. All the flexible tubes 141a, 141b, 141c are coupled (at their proximal ends with respect to the pressurizing unit 140) with a T-connector 144, which comprises a plug for insertion in a corresponding port of the pressurizing unit 140. The transfer set 135 is a disposable element to be changed periodically (for example, every 12 hours).

The pressurizing unit 140 comprises an electric motor (not visible in the figure) of a peristaltic pump, which is used to pressurize the medical fluids (received from the containers 105a, 105b, 105c via the transfer set 135) for their injection into the patient (for example, up to a pressure of 8 bar or at a flow rate from 0.5 to 9.9 ml/s).

A delivery set 145 connects the pressurizing unit 140 to the patient for delivering the (pressurized) medical fluids thereto. The delivery set 145 comprises a delivery line made of a flexible tube 146, which is provided (at a distal end thereof with respect to the patient) with the peristaltic pump, denoted with the reference 147, to be introduced into a dedicated port provided in the pressurizing unit 140 and also to be put in fluid communication with the T-connector 144. The peristaltic pump 147 houses a rotor having a plurality of squeezing wheels, among which a corresponding portion of the flexible tube 146 is inserted. When the delivery set 145 is of single use type (not shown in the figure) for use by a single patient, the flexible tube is longer (than the flexible tube 146 shown in the figure) and it is provided (at a proximal end thereof with respect to the patient) with a connection element for mating with a connection element (for example, a plug) of a peripheral catheter (not shown in the figure), which is inserted through the skin into a peripheral vein of the patient. Instead, when the delivery set 145 is of multiple use type (as shown in the figure) for use by multiple patients, the flexible tube 146 is shorter and it is provided at the proximal end thereof with a connection element 148 for mating with a connection element 150 of an additional patient line made of a (longer) flexible tube 151 (only partially shown in the figure), which in turn ends with a connection element 152 for mating with the connection element of the peripheral catheter. The delivery set 145 is a disposable element, which in case of single use is for use entirely with a single patient and in case of multiple use is to be changed periodically (for example, every 12 hours) but with the patient line 150-152 for use with a single patient only.

A control unit 155 controls operation of the injection system 100. For example, the control unit 155 comprises a (main PCB) board with a microprocessor, a RAM that is used as a working memory by the microprocessor and a flash EPROM that stores information to be preserved even when a power supply is off (particularly, a control program of the injection system 100). Moreover, the control unit 155 comprises a touch-screen and several buttons, which are used by an operator to interact with it.

The injection system 100 is supported by a stand 160. The stand 160 is provided with wheels to facilitate moving the injection system 100; moreover, the wheels have a foot brake to secure the injection system 100 in position.

In operation, for each scan examination to be performed, the operator positions the injection system 100 close to the patient and then turns it on. If it has not already been done, the operator installs the transfer set 135 by inserting each reservoir 142a, 142b and connection element 143a, 143b into the corresponding bottle holder 115a, 115b (across a flap thereof) and releasably blocking them therein (for example, through a snap fitting mechanism). When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 by entering specific information relating to the saline solution of the pouch 110c (for example, its brand name and volume). Otherwise, if the pouch 110c is not used, the operator enters a corresponding command to the control unit 155. In both cases, when the bottle 110a (with the contrast agent) is not installed, the control unit 155 displays a message on its screen prompting the operator to do so. In response thereto, the operator takes the bottle 110a from a separate warmer (not shown in the figure), wherein the bottle 110a has been pre-warmed to a target temperature; the target temperature is set to a value high enough to allow injecting the contrast agent efficiently (for example, at the desired flow rate) and comfortably for the patient, but not too high to be harmful for the patient (for example, 32-37.5° C.). The operator pierces a seal of the bottle 110a with the spike of the bottle connector 130a. The operator then turns the bottle 110a (with the bottle connector 130a connected thereto) up-side-down, inserts the bottle connector 130a into the connection port 132a (so as to connect its connection element to the connection element 143a), mounts the protective cover 120a on the bottle holder 115a (so as to safely enclose the bottle 110a) and fills the reservoir 142a completely with the contrast agent (by repeatedly squeezing the reservoir 142a). At this point, the operator programs the control unit 155 by entering specific information relating to the contrast agent of the bottle 110a (for example, its brand name and volume). The operator repeats the same operations, if it is necessary, to install the bottle 110b (with the contrast agent or with the saline solution). The control unit 155 now displays a message on its screen prompting the operator to install the delivery set 145. In response thereto, the operator inserts the peristaltic pump 147 into the corresponding port of the pressurizing unit 140 and connects the peristaltic pump 147 to the T-connector 144. When the delivery set 145 is for multiple use, the operator further connects the connection element 150 of the patient line 150-152 to the connection element 148 of the delivery line 146-148. The operator now separately primes each transfer line 141a-143a, 141b-143b and 141c-143c by selecting a corresponding priming function on the control unit 155, so as to eliminate any air bubbles that are possibly present within the transfer lines 141*a*-143*a*, 141*b*-143*b* and 141*c*-143*c*, the delivery line 146-148 and/or the (possible) patient line 150-152. Once this priming phase has been terminated (with no air that is sensed in the injection system 100 any longer), the operator finally connects the connection element 152 (or the connection element of the delivery line in case of single use) to the connection element of the peripheral catheter (already introduced into the patient).

At this point, the operator programs the control unit 155 by entering information relating to the scan examination (for example, a gauge of the needle of the peripheral catheter, an injection profile comprising one or more phases each one defined by the type, volume and flow rate of the medical fluids, possibly selected among pre-defined injection profiles for different types of scan examinations) and then starts the scan examination. At the end of the scan examination, the operator turns the injection system 100 off, disconnects the delivery/patient line of the delivery set 145 from the peripheral catheter, and then removes and discards it.

Figure 2:
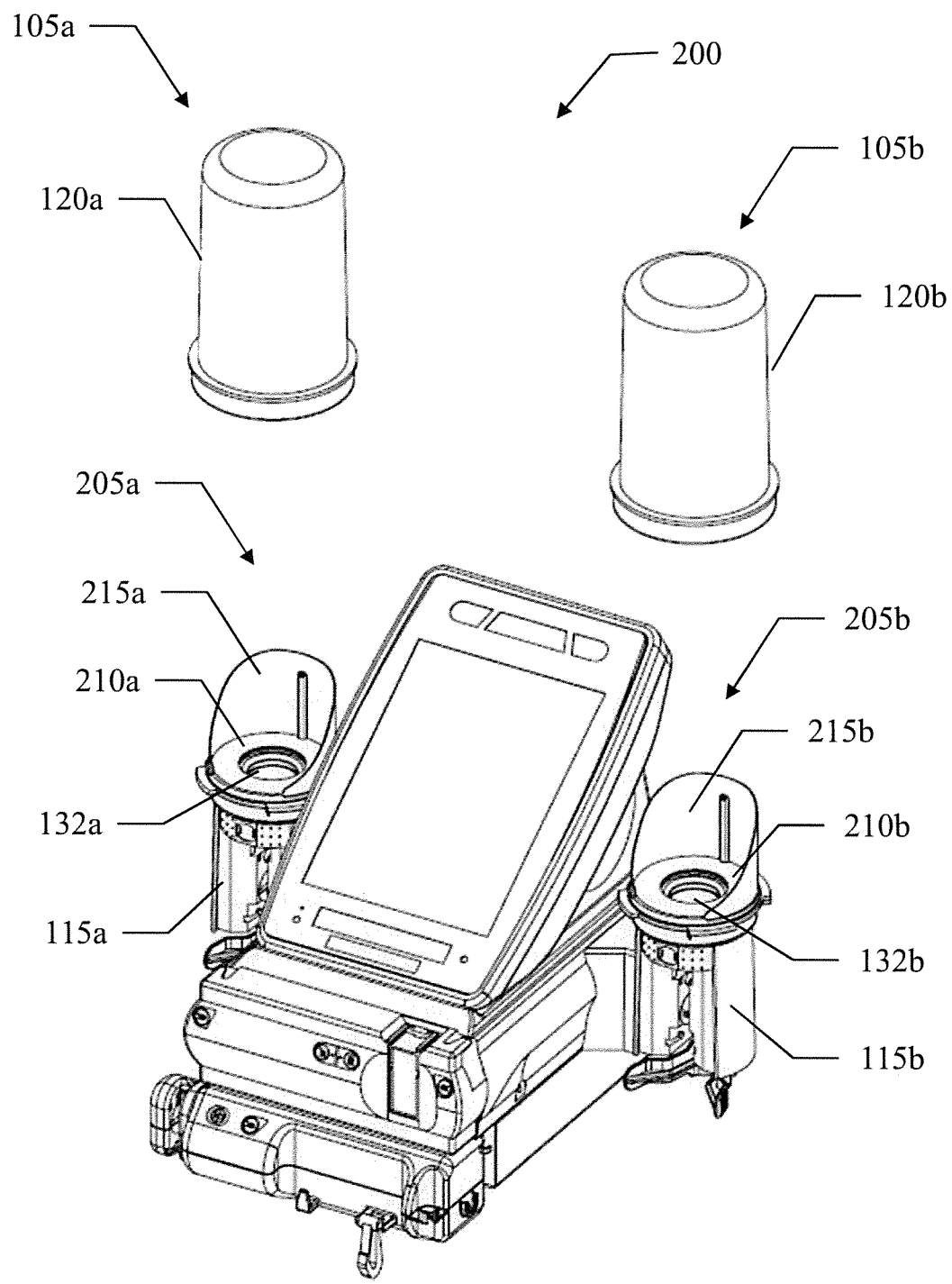
FIG. 2 shows a pictorial representation of a particular of an injection system according to an embodiment of the present disclosure.

With reference now to FIG. 2, a pictorial representation is shown of a particular of an injection system 200 according to an embodiment of the present disclosure.

The injection system 200 differs from the one described above (with respect to FIG. 1) for the addition of a heating device 205*a* and a heating device 205*b* in the supply station 105*a* and in the supply station 105*b*, respectively. Each heating device 205*a*,205*b* is arranged inside the closed chamber defined by the protective cover 120*a*,120*b* mounted on the bottle holder 115*a*,115*b* to maintain the medical fluid contained in the bottles (not shown in the figure) at the target temperature.

In the solution according to an embodiment of the present disclosure, the heating device 205*a*,205*b* comprises two distinct heating elements (for example, implemented by corresponding resistors) that are positioned externally to the bottle 110*a*,110*b* and inside (internally to) the closed chamber defined by the housing means, i.e. by the combination of the bottle holder 115*a*,115*b* and the respective protective cover 120*a*,120*b*. Particularly, a first heating element 210*a*, 210*b* extends around the connection port 132*a*,132*b*, and a second heating element 215*a*,215*b* extends transversally to the first heating element 210*a*,210*b*.

The above-described configuration of the heating device 205*a*,205*b* significantly improves its performance; particularly, this allows maintaining the medical fluid at the target temperature efficiently (with higher uniformity and lower power consumption).

Figure 3A:
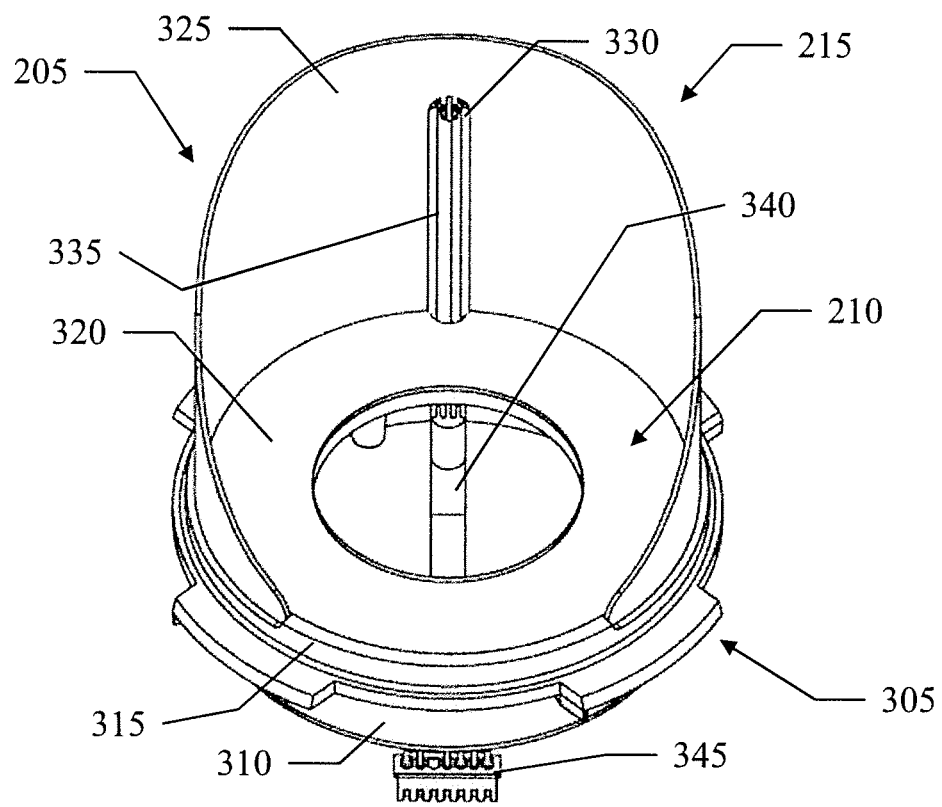
FIG. 3A-FIG. 3B show a pictorial representation in top view and in bottom view, respectively, of a heating device according to an embodiment of the present disclosure, FIG. 4 show a pictorial representation of a heating element according to an embodiment of the present disclosure, FIG. 5 show a pictorial representation of another heating element according to an embodiment of the present disclosure.
Figure 3B:
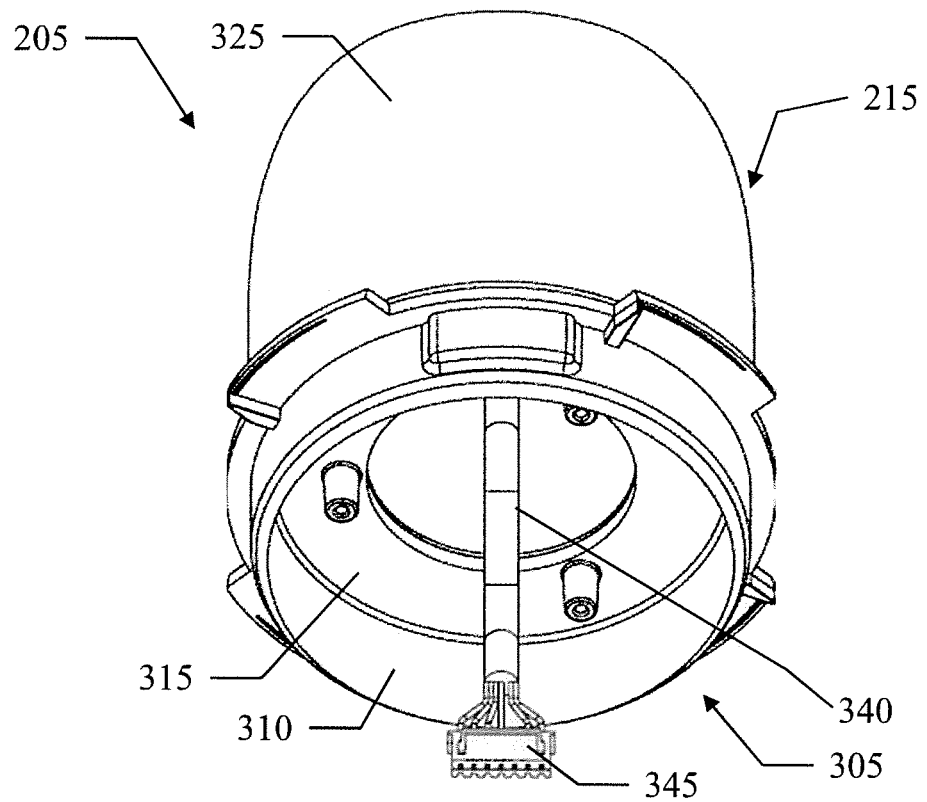

With reference now to FIG. 3A-FIG. 3B together, a pictorial representation is shown in top view and in bottom view, respectively, of a heating device according to an embodiment of the present disclosure (for the sake of simplicity, hereinafter all the elements relating to the two supply stations will be denoted by removing the respective suffixes "a" and "b").

The heating device 205 comprises a stand 305 (for example, made of polycarbonate). As described in the following, the stand 305 is configured for mounting on the bottle holder and for mounting the protective cover (not shown in the figure) on it, instead of on the bottle holder. For example, the stand 305 comprises a crown 310, which is shaped generically as a hollow cylinder (for example, with a diameter of 3-5 cm, a height of 0.5-1.5 cm and a thickness of 0.5-1 cm). The crown 310 is open at its lower end, whereas it is closed at its upper end by a flat ring 315 (for example, having a thickness of 0.5-1 cm). The ring 315 is defined by a disk with a through-hole opened at the center thereof, which through-hole matches the connection port of the bottle holder (for example, with a diameter of 1.5-2.5 cm).

The first heating element 210 (only visible in FIG. 3A) comprises a ring 320 of electrical insulating material (for example, polycarbonate), and it is hereinafter referred to as ring heater 210. The ring 320 is flat (i.e., with a dimension far lower than the other ones, for example, with a thickness of 0.3-0.7 cm and a diameter of 3-5 cm). The ring 320 matches the ring 315 (i.e., it is defined by a disk with a corresponding through-hole opened at the center thereof). The ring 320 is fixed (for example, glued) on the ring 315, and more specifically within a corresponding seat (defined by a depression extending from an upper surface of the ring 315) so as to be flush with it (horizontally in an operative condition). A positioning notch is formed at an outer border of the ring 320 matching a reference tooth provided in the seat of the ring 315 to ensure a correct alignment of the ring 320.

The second heating element 215 comprises a thin fin 325 (for example, with a thickness of 0.3-0.7 cm) of electrical insulating material (for example, polycarbonate), and it is hereafter referred to as fin heater 215. The fin 325 has a plan development with a (lower) base (for example, with a length of 7-10 cm) and a rounded, dome-shaped (upper) profile (for example, with a height ranging from 2-5 cm at the center to 0.1-0.5 cm at the ends of the base). A tab (not visible in the figure) extends downwards at the center of the base (for example, with a height of 0.4-0.6 cm and a width of 0.6-1.0 cm). The fin 325 is curved (along its base) to match a (circumferential) outline of the ring 320. The fin 325 is shorter than the outline of the ring 320; therefore, the fin 325 (once curved) extends along a circular arc subtending an angle lower than 360°, for example, equal to 220°-340°, preferably 240°-320° and still more preferably 260°-300°, such as 280°. The fin 325 is mounted on the stand 305 (vertically in an operative condition) with its base inserted into a corresponding groove provided in the upper surface of the ring 315 (adjacent to the ring 320) and with its tab inserted in a corresponding seat provided in a lateral surface of the crown 310, and then it is fixed (for example, glued) thereon.

The specific arrangement of the (ring and fin) heaters 210,215 described above further improves their performance.

One or more temperature sensors 330 (for example, a main one and a redundant one) are fixed on the fin 325, close to an apex thereof. For example, the temperature sensors 330 are placed on an inner surface of the fin 325 that faces the bottle (not shown in the figure) in an operative condition. The temperature sensors 330 are soldered at a free end of corresponding (electrically) connection tracks 335 (for example, made of copper) that extend vertically along the fin 325 on an outer surface thereof. A cabling (or wiring) system 340 (for example, galvanically insulated by opto-couplers to avoid ground loops) electrically connects the ring heater 210, the fin heater 215 and the connection tracks 335 (and then the sensors 330) to an electrical connector 345.

Figure 4:
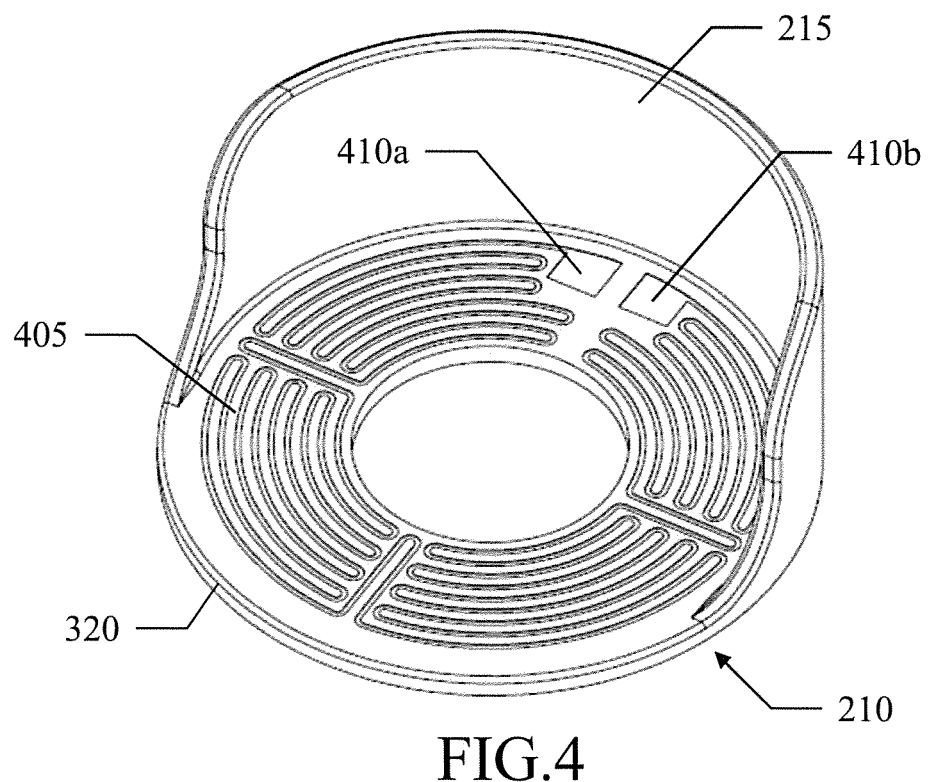

With reference now to FIG. 4, a pictorial representation is shown of the ring heater 210 according to an embodiment of the present disclosure.

The ring heater 210 (shown in combination with the fin heater 215) comprises a heating coil 405, which is formed by a resistor embedded in the ring 320 for generating heat by the Joule effect. The heating coil 405 is made of an (electrical) resistive material (for example, nickel-chrome). The heating coil 405 has a resistance preferably of 30-200Ω, more preferably of 50-150Ω and still more preferably of 80-120Ω, such as 100Ω. For example, the heating coil 405 is formed by a track that is arranged in four sectors, in each one of them extending along two-way concentric arcs. Each sector is connected to the adjacent one via a two-way radial segment. The heating coil 405 ends (in an outer portion of two adjacent sectors) with two pads 410a and 410b, which are exposed on a lower surface of the ring 320 for connecting the heating coil 405 electrically to the cabling system (not shown in the figure). Therefore, the first heating element (i.e. the ring heater) 210 comprises a planar (i.e. flat) arrangement of the heating coil 405 about the connection port 132a,132b. In other words, the heating coil 405 of the first heating element 210 is arranged in a plane which is substantially perpendicular to the longitudinal axis of the bottle holder 115a,115b (and thus also substantially perpendicular to the longitudinal axis of the bottle 110a,110b received by the bottle holder 115a,115b). Thus the heating coil 405 is placed externally to the bottle 110a,110b and it surrounds a limited area of the bottle external surface in proximity of the bottle neck.

Figure 5:
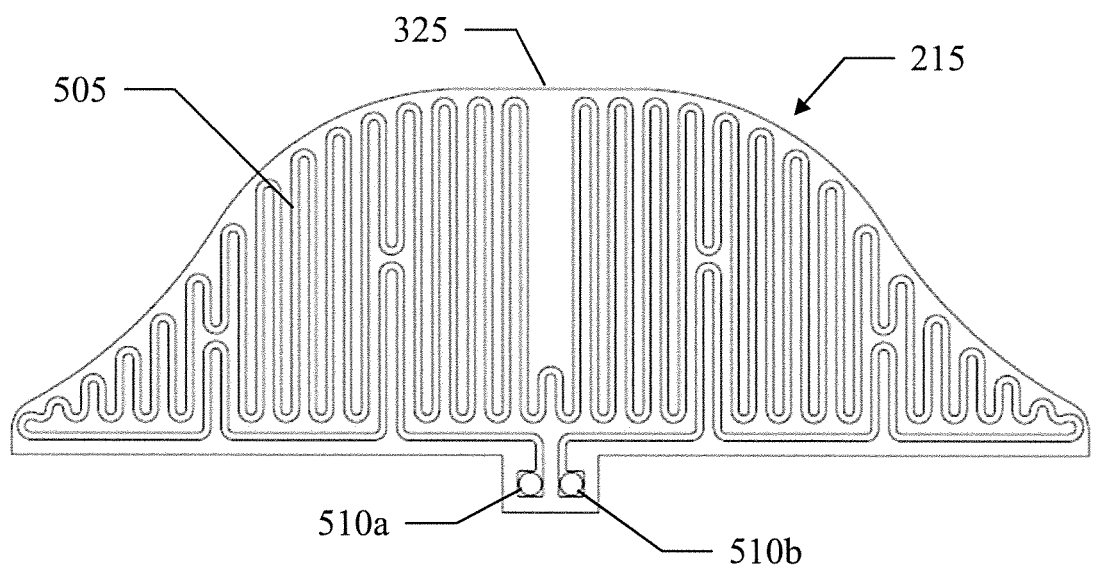

With reference now to FIG. 5, a pictorial representation is shown of the fin heater 215 according to an embodiment of the present disclosure.

In this case as well, the fin heater 215 comprises a heating coil 505, which is formed by a resistor embedded in the fin 325 for generating heat by the Joule effect. The heating coil 505 is made of an (electrical) resistive material (for example, again nickel-chrome). The heating coil 505 has a higher resistance, for example, equal to preferably 2-8 times, more preferably 3-7 times and still more preferably 4-6 times, such as 5 times the resistance of the ring heater, not shown in the figure (for example, preferably 300-700Ω, more preferably 400-600Ω and still more preferably 450-550Ω, such as 500Ω). For example, the heating coil 505 is formed by a track that extends along the base of the fin 325 with some peaks of decreasing height moving towards its ends and then along two-way vertical segments, leaving a portion of the fin 325 free in correspondence to the temperature sensors and the corresponding connection tracks (not shown in the figure). The heating coil 505 ends (in the tab of the fin 325) with two pads 510a and 510b, which are exposed on an inner surface of the fin 325 for connecting the heating coil 505 electrically to the cabling system (not shown in the figure). Therefore, the second heating element (i.e. the fin heater) 215 comprises a curved arrangement of the heating coil 505 to substantially match the bottle external surface, without touching it (i.e. while being spaced apart from it). The heating coil 505 is thus placed externally to the bottle 110a,110b and it is positioned at a given distance therefrom.

The above-described structure of the (ring and fin) heaters is simple, but at the same time very effective.

With reference now to FIG. 6, an exemplary installation is shown of the heating device 205 according to an embodiment of the present disclosure.

The protective cover 120 is configured for mounting on the bottle holder 115 of a standard injection system (without the heating device 205). For example, the bottle holder 115 and the protective cover 120 implement a bayonet-type mount. Particularly, the bottle holder 115 comprises an enclosure 605 (for example, with a generically cylindrical shape) having a lateral opening for receiving and housing the reservoir and the connection element of the corresponding transfer line (not shown in the figure). A through-hole is formed on top of the enclosure 605 to define the connection port 132 for receiving the corresponding bottle connector (not shown in the figure). A cap 610 is mounted (for example, glued or screwed) on top of the enclosure 605. The cap 610 has a through-hole matching the one of the enclosure 605, and it is provided with a male bayonet connector 615. The male bayonet connector 615 comprises a plurality of tabs (for example, four) that project radially outwards; one of the tabs is provided with a stop tooth that projects downwards from an end thereof. The protective cover 120 comprises a matching female bayonet connector 620 integral thereto. The female bayonet connector 620 comprises the same number of tabs (matching the ones of the male bayonet connector 615) that project radially inwards from a free (lower) border of the protective cover 120. The clearings that are formed between each pair of adjacent tabs of the protective cover 120 define corresponding receptors for the tabs of the male bayonet connector 615. The female bayonet connector 620 further comprises a rim that projects radially inwards along the entire protective cover 120 at an inner position. The rim is spaced apart from the tabs by a distance corresponding to a thickness of the tabs of the male bayonet connector 615, so as to define a gap for receiving them.

The protective cover 120 may be mounted on the bottle holder 115 by placing the protective cover 120 over the bottle holder 115, aligning the receptors of the female bayonet connector 620 with the tabs of the male bayonet connector 615 (dismount condition) and translating (lowering) the protective cover 120 with the receptors of the female bayonet connector 620 that slide along the tabs of the male bayonet connector 615 until the latter ones abut against the rim of the female bayonet connector 620 (interference condition). At this point, the protective cover 120 is rotated (screwed), for example, by 45°, thereby causing the tabs of the male bayonet connector 615 to enter the gaps of the female bayonet connector 620, until the stop tooth of the male bayonet connector 615 (arranged upstream the corresponding tab along a rotation direction) abuts against one of the tabs of the female bayonet connector 620 (mount condition). The same operations are repeated in reverse order to remove the protective cover 120 from the bottle holder 115.

In the solution according to an embodiment of the present disclosure, the heating device 205 replaces the cap 610. For this purpose, the stand 305 is provided with a plurality of pegs 622, for example, three (only two visible in the figure) that project downwards from the ring 315. The pegs 622 match corresponding holes 625 that are already provided on top of the enclosure 605 (for receiving similar pegs of the cap 610, not visible in the figure). Moreover, a window 630 is opened at the top of the enclosure 605 for inserting the electrical connector 345 and a corresponding portion of the cabling system 340. The crown 310 is provided with a male bayonet connector 635 substantially the same as the male bayonet connector 615 (i.e., comprising the same number of tabs that project radially outwards, with one of the tabs that is provided with a stop tooth that projects downwards from an end thereof). The heating device 205 is mounted on the enclosure 605 (without the cap 610) by passing the electrical connecter 345 through the window 630 and then plugging it into a corresponding connector (not shown in the figure), which is (electrically) connected to a controller 640 of the heating device 205 (for example, housed in the control unit of the injection system, not shown in the figure). For example, the controller 640 is implemented with a (daughter PCB) board mounting a microprocessor, a RAM that is used as a working memory by the microprocessor and a flash EPROM that stores information to be preserved even when a power supply is off (particularly, a control program of the heating device 205). At this point, the heating device 205 is fitted on top of the enclosure 605 and fixed thereto (for example, glued or screwed as above). As a result, the protective cover 120 may be mounted on the heating device 205 exactly in the same way as on the bottle holder 115 with the cap 610 (with the female bayonet connector 620 that now mates with the male bayonet connector 635).

In this way, the injection system with the heating device 205 stays compatible with previous injection systems without it.

In operation, the controller 640 supplies the heating device 205 (for example, at 20-40V). The controller 640 continually monitors the temperatures measured by both the main temperature sensor and the redundant temperature sensor of the heating device 205 (for safety reasons). If the difference between the measured temperatures exceeds a threshold value (for example, 0.3-1° C.) for two (or more) consecutive measures (to improve robustness), the controller 640 enters an error condition (for example, by sending an error message to the control unit of the injection system, causing it to stop operation of the injection system and to provide a warning message to the operator). Otherwise, the controller 640 drives the heating device 205 with hysteresis (to reduce a frequency of its switching). Particularly, assuming that at the beginning the temperature measured by the main temperature sensor is lower than the target temperature minus a delta temperature (for example, 0.5-1 2° C.), the controller 640 switches the heating device on. For this purpose, the controller 640 may control the ring heater and the fin heater either individually or together. For example, the controller 640 may generate a (common) control signal corresponding to the difference between the target temperature and the measured temperature, which control signal is translated to a same PWM power signal that directly drives both the ring heater and the fin heater. As indicated above, the resistance of the fin heater is higher than the resistance of the ring heater, so that the fin heater converts more electric power into heat than the ring heater does (for example, 10-12 W and 2-4 W, respectively, when they are driven by a same current of 0.3-0.7 mA). The difference heating provided by the ring heater and the fin heater further improves the performance of the heating device. At the same time, the controller 640 starts verifying whether the measured temperature exceeds the target temperature plus the same delta temperature. As soon as this occurs, the controller 640 switches the heating device off. At this point, the controller 640 starts verifying whether the measured temperature falls below the target temperature minus the delta temperature. As soon as this occurs, the controller 640 switches the heating device on again, so as to repeat the same operations continually. As a result, the temperature in the chamber formed between the bottle holder 115 and the protective cover 120 swings around the target temperature in a range defined by the delta temperature.

Modifications

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides an injection system. However, the injection system may be of any type, of syringe-type as well (for example, with another pressurizing system, with a ceiling mount for mounting it on the ceiling of an imaging suite).

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected from a container. However, the injection system may comprise any number of supply stations (down to a single one) for supplying the same or different fluids (in any combination); moreover, the container may be of any type, either the same or different in the supply stations (for example, bottles, bags, pouches, syringes and any combination thereof).

In an embodiment, at least one of the supply stations comprises housing means defining a chamber for housing the container. However, the above-described solution may be applied to any number of supply stations (from a single one to all of them); moreover, the chamber may be of any type, shape, size and arranged at any position (for example, enclosing the container completely or only partially, with a hook for hanging it) and it may be defined by any structure (for example, an enclosure with an access door).

In an embodiment, the chamber has a connection port for connecting the container to a delivery arrangement for delivering the fluid to the patient. However, the connection port may be of any type, shape, size and arranged at any position (for example, a valve integral with the bottle holder); moreover, the delivery arrangement may be of any type (for example, with individual transfer lines for each supply station, with a delivery line ending with a needle for direct insertion into the patient).

In an embodiment, said at least one supply station comprises a conditioning device for thermally conditioning the fluid in the chamber. However, the conditioning device may operate in any way (for example, to heat and/or to cool the fluid starting from any temperature, like the room temperature).

In an embodiment, the conditioning device comprises a first conditioning element arranged around the connection port. However, the first conditioning element may be of any type, shape and size (for example, squared) and it may be arranged around the connection port in any way (for example, only partially surrounding it).

In an embodiment, the conditioning device comprises a second conditioning element extending transversally to the first conditioning element. However, the second conditioning element may be of any type, shape and size (for example, U-like) and it may extend transversally to the first conditioning element in any way (for example, obliquely, completely surrounding it).

In an embodiment, the first conditioning element extends horizontally in an operative condition of the injection system. However, the possibility of having the first conditioning element extending in another direction is not excluded (for example, vertically when the connection port is arranged laterally).

In an embodiment, the second conditioning element extends from a border of the first conditioning element. However, the second conditioning element may be arranged at any other position (either in contact with or spaced apart from the first conditioning element).

In an embodiment, the second conditioning element extends vertically in the operative condition of the injection system. However, the possibility of having the second conditioning element extending in another direction is not excluded (for example, horizontally when the connection port is arranged laterally).

In an embodiment, the first conditioning element completely surrounds the connection port in a plan view. However, the first condition element may surround the connection port in any way (for example, completely or only partially along its height).

In an embodiment, the first conditioning element comprises a ring that is formed by a disk having a through-hole matching the connection port. However, the ring may have any thickness and it may be formed by a disk having any size and with any through-hole matching the connection port in any way (for example, slightly narrower or larger than it).

In an embodiment, the second conditioning element partially surrounds the connection port. However, the second condition element may be arranged in any way around the connection port (for example, with multiple components distributed along its border).

In an embodiment, the second conditioning element extends along a circular arc. However, the second conditioning element may extend along any line (for example, with an elliptical shape).

In an embodiment, the circular arc subtends an angle of 220°-340°. However, the circular arc may have any other extent.

In an embodiment, the second conditioning element comprises a fin having a height decreasing from a center of the fin to each end thereof. However, the height of the fin may decrease in any way (for example, with one or more sections at constant height); more generally, the fin may have any other profile (even always with the same height).

In an embodiment, the first conditioning element comprises a first heating coil having a first resistance and the second conditioning element comprises a second heating coil having a second resistance higher than the first resistance. However, the heating coils may be of any type, shape and size; moreover, they may have any resistance, in either absolute or relative terms (with any one of them lower than, equal to or higher than the other one). More generally, any other implementation of the heating elements is contemplated (even not based on the Joule effect).

In an embodiment, the housing means comprises a holder for holding the container. However, the holder may be of any type, shape and size (for example, with a mechanical lock for the container).

In an embodiment, the housing means comprises a cover for covering the container when it is held on the holder. However, the cover may be of any type, shape and size (for example, a cap hinged to the holder).

In an embodiment, at least one supply station comprises means for mounting the conditioning device on the holder. However, the conditioning device may be mounted on the holder in any way (for example, with a snap fitting), either in addition or in alternative to its connector for the cover (which may also be completely missing when the supply station is specifically designed for use with the conditioning device only).

In an embodiment, the conditioning device comprises a first connector and the cover comprises a second connector for mating with the first connector. However, the connectors may be of any type (for example, based on one or more clips). In any case, the cover may be the same that is used without the conditioning device or it may also be specifically designed for use with the conditioning device.

In an embodiment, the injection system comprises means for controlling the first conditioning element and the second conditioning element individually. However, the conditioning elements may be controlled either individually or always in the same way. Moreover, the control of the conditioning device may be implemented in any way. For example, the conditioning device may be controlled by any software program suitable to be used by any data processing or computing system or in connection therewith (for example, directly in the central unit) thereby configuring the system to perform the desired operations (for example, in the form of external or resident software, firmware, or microcode). The program may be provided on any computer readable storage medium or it may be downloaded to the corresponding computing system in any way (for example, via a network). In any case, the heating device may be controlled with a hardware structure (for example, a circuity integrated in one or more chips) or with a combination of software and hardware suitably programmed or otherwise configured.

In an embodiment, the conditioning device comprises a plurality of temperature sensors each one for measuring a temperature in the chamber. However, the temperature sensors may be of any type, at any position and in any number (down to none).

In an embodiment, the injection system comprises means for detecting an error condition according to a comparison of the measured temperatures. However, the detection of the error condition may be implemented in any way (as above); moreover, the error condition may be detected according to any comparison of the measured temperatures (for example, according to a trend of their difference over time). In any case, this feature may also be omitted at all (for example, when a single temperature sensor is available).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

In an embodiment, the conditioning device is a heating device for maintaining a target temperature in the chamber. However, the control of the temperature may be implemented in any way (as above); moreover, the target temperature may be maintained in any way within any range around any desired value (for example, by switching the heating device on when the measured temperature falls below the target temperature possibly minus a delta temperature and switching the heating device off when the measured temperature exceeds the target temperature possibly plus the delta temperature).

An embodiment provides a conditioning device for use in the injection system described above; the conditioning device comprises said first conditioning element and said second conditioning element. However, the conditioning device may be put on the market as a stand-alone product to be used with pre-existing injection systems, as a modification (after-market) kit for application thereto or directly integrated in (new) injection systems.

Generally, similar considerations apply if the injection system and the conditioning device each has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a method for operating an injection system for injecting one or more fluids into a patient. For at least one supply station comprised in the injection system (for supplying one of the fluids to be injected from a container) the method comprises housing the container in a chamber (with the container connected to a delivery arrangement for delivering the fluid to the patient through a connection port of the chamber) and conditioning the medical fluid thermally in the chamber; said step of conditioning comprises conditioning the fluid thermally by a first conditioning element arranged around the connection port and by a second conditioning element extending transversally to the first conditioning element.

The above-described steps only relate to a control method of the injection system, which is completely independent of the actual injection of the fluids into the patient; in any case, the injection may also be performed in a non-invasive manner without any substantial physical intervention on the patient that would require professional medical expertise or entail any health risk for the patient (for example, intramuscularly). Therefore, this method is merely directed to the operation of the injection system without itself providing any functional interaction with the effects produced by the injection system on the patient.

Generally, similar considerations apply if the same solution is implemented with an equivalent method by using similar steps with the same functions of more steps or portions thereof, removing some steps being non-essential, or adding further optional steps); moreover, the steps may be performed in a different order, concurrently or in an interleaved way (at least in part).

The invention claimed is:

1. An injection system (200) for injecting one or more fluids into a patient, the injection system (200) comprising one or more supply stations (105a;105b) each one for supplying one of the fluids to be injected from a container (110a;110b), wherein at least one of the supply stations (105a;105b) comprises:
    housing means (115a,120a;115b,120b) defining a chamber for housing the container (110a;110b), the chamber having a connection port (132a;132b) for connecting the container (110a;110b) to a delivery arrangement (135,145) for delivering the fluid to the patient, and
    a conditioning device (205a;205b) for thermally conditioning the fluid in the chamber,
    characterized in that
    the conditioning device (205a;205b) comprises a first conditioning element (210a;210b) arranged around the connection port (132a;132b) and a second conditioning element (215a;215b) extending transversally to the first conditioning element (210a;210b),
    wherein the first conditioning element (210a;210b) at least partially surrounds the connection port (132a;132b) in a plan view,
    wherein the first conditioning element (210a;210b) comprises a ring (320) formed by a disk having a through-hole matching the connection port (132a;132b).

2. The injection system (200) according to claim 1, wherein the first conditioning element (210a;210b) extends horizontally in an operative condition of the injection system (200) and the second conditioning element (215a;215b) extends from a border of the first conditioning element (210a;210b) vertically in the operative condition of the injection system (200).

3. The injection system (200) according to claim 1, wherein the second conditioning element (215a;215b) partially surrounds the connection port (132a;132b).

4. The injection system (200) according to claim 3, wherein the second conditioning element (215a;215b) extends along a circular arc subtending an angle of 220°-340°.

5. The injection system (200) according to claim 1, wherein the second conditioning element (215a;215b) comprises a fin (325) having a height decreasing from a center of the fin (325) to each end thereof.

6. The injection system (200) according to claim 1, wherein the first conditioning element (210a;210b) comprises a first heating coil (405) having a first resistance and the second conditioning element (215a;215b) comprises a second heating coil (415) having a second resistance higher than the first resistance.

7. The injection system (200) according to claim 1, wherein the housing means (115a,120a;115b,120b) comprises a holder (115;115b) for holding the container (110a;110b) and a cover (120a;120b) for covering the container (110a;110b) when held on the holder (115a;115b), and wherein at least one supply station (105a;105b) comprises means (622,625) for mounting the conditioning device (205a;205b) on the holder (115;115b), the conditioning device (205a;205b) comprising a first connector (635) and the cover (120a;120b) comprising a second connector (620) for mating with the first connector (635).

8. The injection system (200) according to claim 1, comprising means (640) for controlling the first conditioning element (210*a*;210*b*) and the second conditioning element (215*a*;215*b*) individually.

9. The injection system (200) according to claim 1, wherein the conditioning device (205*a*;205*b*) comprises a plurality of temperature sensors (330) each one for measuring a temperature in the chamber, the injection system (200) comprising means (640) for detecting an error condition according to a comparison of the measured temperatures.

10. The injection system (200) according to claim 1, wherein the injection system (200) is for injecting the fluids into the patient during a scan examination thereof, the fluids being one or more medical fluids comprising a contrast agent and/or a saline solution.

11. The injection system (200) according to claim 1, wherein the conditioning device (205*a*;205*b*) is a heating device (205*a*;205*b*) for maintaining a target temperature in the chamber.

12. A method for operating an injection system (200) for injecting one or more fluids into a patient, wherein for at least one supply station (105*a*;105*b*) comprised in the injection system (200) for supplying one of the fluids to be injected from a container (110*a*;110*b*) the method comprises:
   housing the container (110*a*;110*b*) in a chamber with the container (110*a*;110*b*) connected to a connection port (132*a*;132*b*) for connecting the container (110*a*;110*b*) to a delivery arrangement (135,145) for delivering the fluid to the patient, and
   conditioning the fluid thermally in the chamber,
characterized in that
said conditioning comprises:
   conditioning the fluid thermally by a first conditioning element (210*a*;210*b*) arranged around the connection port (132*a*;132*b*) and by a second conditioning element (215*a*;215*b*) extending transversally to the first conditioning element (210*a*;210*b*),
   wherein the first conditioning element (210*a*;210*b*) at least partially surrounds the connection port (132*a*; 132*b*) in a plan view,
   wherein the first conditioning element (210*a*;210*b*) comprises a ring (320) formed by a disk having a throughhole matching the connection port (132*a*;132*b*).

13. An injection system (200) for injecting one or more fluids into a patient, the injection system (200) comprising one or more supply stations (105*a*;105*b*) each one for supplying one of the fluids to be injected from a container (110*a*;110*b*), wherein at least one of the supply stations (105*a*;105*b*) comprises:
   housing means (115*a*,120*a*;115*b*,120*b*) defining a chamber for housing the container (110*a*;110*b*), the chamber having a connection port (132*a*;132*b*) for connecting the container (110*a*;110*b*) to a delivery arrangement (135,145) for delivering the fluid to the patient, and
   a conditioning device (205*a*;205*b*) for thermally conditioning the fluid in the chamber,
   characterized in that
   the conditioning device (205*a*;205*b*) comprises a first conditioning element (210*a*;210*b*) arranged around the connection port (132*a*;132*b*) and a second conditioning element (215*a*;215*b*) extending transversally to the first conditioning element (210*a*;210*b*), wherein the injection system (200) comprises means (640) for controlling the first conditioning element (210a;210*b*) and the second conditioning element (215*a*;215*b*) individually.

14. The injection system (200) according to claim 13, wherein the first conditioning element (210*a*;210*b*) extends horizontally in an operative condition of the injection system (200) and the second conditioning element (215*a*;215*b*) extends from a border of the first conditioning element (210*a*;210*b*) vertically in the operative condition of the injection system (200).

15. The injection system (200) according to claim 13, wherein the second conditioning element (215*a*;215*b*) partially surrounds the connection port (132*a*;132*b*).

16. The injection system (200) according to claim 15, wherein the second conditioning element (215*a*;215*b*) extends along a circular arc subtending an angle of 220°-340°.

17. The injection system (200) according to claim 13, wherein the second conditioning element (215*a*;215*b*) comprises a fin (325) having a height decreasing from a center of the fin (325) to each end thereof.

18. The injection system (200) according to claim 13, wherein the first conditioning element (210*a*;210*b*) comprises a first heating coil (405) having a first resistance and the second conditioning element (215*a*;215*b*) comprises a second heating coil (415) having a second resistance higher than the first resistance.

19. The injection system (200) according to claim 13, wherein the housing means (115*a*,120*a*;115*b*,120*b*) comprises a holder (115;115*b*) for holding the container (110*a*; 110*b*) and a cover (120*a*;120*b*) for covering the container (110*a*;110*b*) when held on the holder (115*a*;115*b*), and wherein at least one supply station (105*a*;105*b*) comprises means (622,625) for mounting the conditioning device (205*a*;205*b*) on the holder (115;115*b*), the conditioning device (205*a*;205*b*) comprising a first connector (635) and the cover (120*a*;120*b*) comprising a second connector (620) for mating with the first connector (635).

20. The injection system (200) according to claim 13, wherein the housing means (115*a*,120*a*;115*b*,120*b*) defines a closed chamber for housing the container (110*a*;110*b*), and wherein the conditioning device (205*a*;205*b*) is positioned externally to said container (110*a*;110*b*) and internally to said closed chamber.

* * * * *